US009708251B2

(12) United States Patent
Allen et al.

(10) Patent No.: US 9,708,251 B2
(45) Date of Patent: Jul. 18, 2017

(54) UNSATURATED FATTY ALCOHOL ALKOXYLATES FROM NATURAL OIL METATHESIS

(71) Applicant: Stepan Company, Northfield, IL (US)

(72) Inventors: David R. Allen, Chicago, IL (US); Marcos Alonso, Chicago, IL (US); Mary Beddaoui, Glenview, IL (US); Randal J. Bernhardt, Antioch, IL (US); Aaron Brown, Chicago, IL (US); Xue Min Dong, Lincolnshire, IL (US); Wilma Gorman, Park Ridge, IL (US); John Hutchison, Chicago, IL (US); Gary Luebke, Chicago, IL (US); Renee Luka, Park Ridge, IL (US); Franz Luxem, Palatine, IL (US); Andrew D. Malec, Chicago, IL (US); Ronald A Masters, Glenview, IL (US); Dennis S Murphy, Libertyville, IL (US); Patti Skelton, Winder, GA (US); Brian Sook, Valdosta, GA (US); Chris Spaulding, Evanston, IL (US); Michael Wiester, Chicago, IL (US); Patrick Shane Wolfe, Palatine, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 14/395,829

(22) PCT Filed: Mar. 13, 2013

(86) PCT No.: PCT/US2013/031060
§ 371 (c)(1),
(2) Date: Oct. 21, 2014

(87) PCT Pub. No.: WO2013/162737
PCT Pub. Date: Oct. 31, 2013

(65) Prior Publication Data
US 2015/0087724 A1 Mar. 26, 2015

Related U.S. Application Data

(60) Provisional application No. 61/637,607, filed on Apr. 24, 2012.

(51) Int. Cl.
| | |
|---|---|
| *A61K 47/00* | (2006.01) |
| *C07C 309/10* | (2006.01) |
| *C11D 1/14* | (2006.01) |
| *C11D 1/29* | (2006.01) |
| *A01N 25/30* | (2006.01) |
| *A61K 8/46* | (2006.01) |
| *B01F 17/00* | (2006.01) |
| *C04B 38/10* | (2006.01) |
| *C07C 29/147* | (2006.01) |

(Continued)

(52) U.S. Cl.
CPC ............ *C07C 309/10* (2013.01); *A01N 25/30* (2013.01); *A61K 8/463* (2013.01); *A61K 8/466* (2013.01); *B01F 17/0057* (2013.01); *B01F 17/0092* (2013.01); *C04B 38/10* (2013.01); *C07C 29/147* (2013.01); *C07C 41/03* (2013.01); *C07C 41/06* (2013.01); *C07C 303/14* (2013.01); *C07C 303/32* (2013.01); *C07C 309/08* (2013.01); *C09D 7/1233* (2013.01); *C11D 1/143* (2013.01); *C11D 1/146* (2013.01); *C11D 1/29* (2013.01); *C11D 1/37* (2013.01); *C11D 1/66* (2013.01); *A61K 2800/10* (2013.01)

(58) Field of Classification Search
None
See application file for complete search history.

(56) References Cited

U.S. PATENT DOCUMENTS

| | | |
|---|---|---|
| 2,865,968 A | 12/1958 | Hansley et al. |
| 3,193,586 A | 7/1965 | Rittmeister |

(Continued)

FOREIGN PATENT DOCUMENTS

| | | | |
|---|---|---|---|
| PL | 130384 | * | 8/1984 |
| WO | 2008048522 | | 4/2008 |

(Continued)

OTHER PUBLICATIONS

Qin et al Journal of the American Chemical Society (2010) 132(46), 16432-16441.*
Second Written Opinion dated May 16, 2016 from Intellectual Property Office of Singapore, 5 pages.
Weil, J. et al.: "Ether alcohol sulfates from oleyl alcohol", database retrieval from Journal of the American Oil Chemists' Society, Abstract, 1 page.
Youn, M. et al.: "The additive effect of polyoxethylene compounds on the photographic characters of photographic emulsion", Journal of Photoscience (2000), Abstract, 1 page.

(Continued)

*Primary Examiner* — Sudhakar Katakam
*Assistant Examiner* — Ana Z Muresan
(74) *Attorney, Agent, or Firm* — Dilworth IP LLC

(57) ABSTRACT

Unsaturated fatty alcohol alkoxylates, processes for making them, and methods of using them are disclosed. In one aspect, a monounsaturated fatty alcohol alkoxylate is made by reducing a metathesis-derived monounsaturated alkyl ester, followed by alkoxylation of the resulting monounsaturated alcohol. Microscopy reveals that the monounsaturated alkoxylates have isotropic and lamellar phases over a wider range of actives levels compared with their saturated analogs. This attribute expands formulating latitude for many end-use applications. The unsaturated fatty alcohol alkoxylates are valuable in, for example, agricultural solvents, nonionic emulsifiers for agricultural compositions, hard surface cleaners, laundry detergents, specialty foams, additives or surfactants for paints or coatings, and surfactant compositions for enhanced oil recovery.

24 Claims, No Drawings

(51) Int. Cl.
*C07C 303/14* (2006.01)
*C07C 303/32* (2006.01)
*C07C 309/08* (2006.01)
*C11D 1/37* (2006.01)
*C07C 41/06* (2006.01)
*C09D 7/12* (2006.01)
*C11D 1/66* (2006.01)
*C07C 41/03* (2006.01)

(56) References Cited

U.S. PATENT DOCUMENTS

| | | | |
|---|---|---|---|
| 3,875,202 | A | 4/1975 | Steckler |
| 4,545,941 | A | 10/1985 | Rosenburg |
| 4,804,790 | A | 2/1989 | Schuett |
| 5,124,491 | A | 6/1992 | Fleckenstein et al. |
| 5,312,940 | A | 5/1994 | Grubbs et al. |
| 5,342,909 | A | 8/1994 | Grubbs et al. |
| 5,482,908 | A | 1/1996 | Le-Khac |
| 5,672,781 | A | 9/1997 | Koehler et al. |
| 5,710,298 | A | 1/1998 | Grubbs et al. |
| 5,728,785 | A | 3/1998 | Grubbs et al. |
| 5,728,917 | A | 3/1998 | Grubbs et al. |
| 5,750,815 | A | 5/1998 | Grubbs et al. |
| 5,811,594 | A | 9/1998 | Schmid et al. |
| 5,831,108 | A | 11/1998 | Grubbs et al. |
| 5,922,863 | A | 7/1999 | Grubbs et al. |
| 6,306,988 | B1 | 10/2001 | Grubbs et al. |
| 6,414,097 | B1 | 7/2002 | Grubbs et al. |
| 6,683,224 | B1 | 1/2004 | Hourticolon et al. |
| 6,696,597 | B2 | 2/2004 | Pederson et al. |
| 6,794,534 | B2 | 9/2004 | Grubbs et al. |
| 7,102,047 | B2 | 9/2006 | Grubbs et al. |
| 7,169,959 | B2 | 1/2007 | Heck et al. |
| 7,208,643 | B2 | 4/2007 | Namba et al. |
| 7,378,528 | B2 | 5/2008 | Herrmann et al. |
| 7,799,333 | B2 | 9/2010 | Bruening et al. |
| 8,481,747 | B2 | 7/2013 | Schrodi |
| 8,501,973 | B2 | 8/2013 | Schrodi et al. |
| 8,569,560 | B2 | 10/2013 | Schrodi et al. |
| 8,614,344 | B2 | 12/2013 | Kaido et al. |
| 8,735,640 | B2 | 5/2014 | Cohen et al. |
| 2003/0139317 | A1 | 7/2003 | Behler et al. |
| 2005/0170968 | A1 | 8/2005 | Berghaus et al. |
| 2009/0264672 | A1 | 10/2009 | Abraham et al. |
| 2010/0145086 | A1 | 6/2010 | Schrodi et al. |
| 2010/0310483 | A1* | 12/2010 | Klug .............. A61K 8/042 424/59 |
| 2010/0311625 | A1 | 12/2010 | Elomari et al. |
| 2011/0028374 | A1 | 2/2011 | Fossum et al. |
| 2011/0098492 | A1 | 4/2011 | Varineau et al. |
| 2011/0113679 | A1 | 5/2011 | Cohen et al. |
| 2012/0035386 | A1 | 2/2012 | Nguyen |
| 2013/0281688 | A1 | 10/2013 | Di Biase et al. |
| 2014/0275506 | A1 | 9/2014 | Littich et al. |
| 2014/0336398 | A1 | 11/2014 | Cohen et al. |
| 2014/0336399 | A1 | 11/2014 | Cohen et al. |

FOREIGN PATENT DOCUMENTS

| | | |
|---|---|---|
| WO | 2012061093 | 5/2012 |
| WO | 2012061095 | 5/2012 |

OTHER PUBLICATIONS

Baumann, W. et al: "Alkoxylipids IV. Synthesis and Characterization of Naturally Occurring Ethers, Esters and Ether Esters of Diols", Biochimica et Biophysica ACTA, Jan. 1, 1967, pp. 355-365.
Dierker, M. et al.: "Surfactants from oleic, erucic and petroselinic acid: Synthesis and properties", European Journal of Lipid Science and Technology, vol. 112, No. 1, Jan. 1, 2010, pp. 122-136.
"Supplementary EP Search Report" dated Jan. 25, 2016, issued by the European Patent Office in corresponding EP Application No. 13781311.9, 11 pages.
J.C. Mol, Green Chem. 4 (2002) 5.
J.C. Mol, Topics in Catal. 27 (2004) 97.
Dijgoué et al., Appl. Catal. A 368 (2009) 158.
R. Subbarao et al., Indian J. Tech. 4 (1966) 153.
Chinese 2nd Notification of Office Action issued Sep. 5, 2016 with Search Report from corresponding CN Application No. 20138033586.5, along with unofficial English translation, 15 pages.

* cited by examiner

UNSATURATED FATTY ALCOHOL ALKOXYLATES FROM NATURAL OIL METATHESIS

FIELD OF THE INVENTION

The invention generally relates to unsaturated fatty alcohol alkoxylates wherein the unsaturated fatty alcohol precursors are made from a metathesis-derived feedstock.

BACKGROUND OF THE INVENTION

Fatty alcohol alkoxylates are versatile surfactants. They are used across a broad array of industries and end uses, including personal care, laundry and cleaning, emulsion polymerization, agricultural uses, oilfield applications, industrial compositions, and specialty foamers.

Fatty alcohols are usually made by reducing the corresponding fatty acids or esters, typically by catalytic hydrogenation. Often, the catalyst includes zinc or copper and chromium. U.S. Pat. No. 5,672,781, for instance, uses a $CuCrO_4$ catalyst to hydrogenate methyl esters from palm kernel oil, which has substantial unsaturation, to produce a mixture of fatty alcohols comprising about 52 wt. % of oleyl alcohol, a monounsaturated fatty alcohol. For additional examples, see U.S. Pat. Nos. 2,865,968; 3,193,586; 4,804,790; 6,683,224; and 7,169,959.

The fatty acids or esters used to make fatty alcohols and their derivatives are usually made by hydrolysis or transesterification of triglycerides, which are typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. The unsaturation in these acids has either exclusively or predominantly cis-configuration.

Recent improvements in metathesis catalysts (see J. C. Mol, *Green Chem.* 4 (2002) 5) provide an opportunity to generate reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. Metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecenes, 9-decenoic acid, and 9-undecenoic acid. Despite the availability (from cross-metathesis of natural oils and olefins) of unsaturated fatty esters having reduced chain length and/or predominantly trans-configuration of the unsaturation, unsaturated fatty alcohol alkoxylates made from these feedstocks appear to be unknown.

In sum, traditional sources of fatty acids and esters used for making unsaturated fatty alcohols generally have predominantly (or exclusively) cis-isomers and lack relatively short-chain (e.g., $C_{10}$ or $C_{12}$) unsaturated fatty portions. Metathesis chemistry provides an opportunity to generate precursors having shorter chains and mostly trans-isomers, which could impart improved performance when the precursors are converted to downstream compositions (e.g., in surfactants).

SUMMARY OF THE INVENTION

The invention relates to fatty alcohol alkoxylates. The alkoxylates are made by reacting alkylene oxides with monounsaturated fatty alcohol compositions, which are in turn made by reducing a metathesis-derived monounsaturated alkyl ester. Microscopy reveals that the monounsaturated alkoxylates have isotropic and lamellar phases over a wider range of actives levels compared with their saturated analogs. This attribute can expand formulating latitude for many end-use applications. The unsaturated fatty alcohol alkoxylates are valuable in, for example, agricultural solvents, nonionic emulsifiers for agricultural compositions, hard surface cleaners, laundry detergents, specialty foams, additives or surfactants for paints or coatings, and surfactant compositions useful for enhanced oil recovery.

DETAILED DESCRIPTION OF THE INVENTION

In one aspect, the invention relates to derivatives made by alkoxylating monounsaturated fatty alcohol compositions. The fatty alcohol compositions are made by reducing a metathesis-derived monounsaturated alkyl ester.

The monounsaturated alkyl ester, preferably a $C_5$-$C_{35}$ alkyl ester, and more preferably a $C_{10}$-$C_{17}$ monounsaturated lower alkyl ester, used as a reactant is derived from metathesis of a natural oil. Traditionally, these materials, particularly the short-chain alkyl esters (e.g., methyl 9-decenoate or methyl 9-dodecenoate), have been difficult to obtain except in lab-scale quantities at considerable expense. However, because of the recent improvements in metathesis catalysts, these esters are now available in bulk at reasonable cost. Thus, the monounsaturated esters are conveniently generated by self-metathesis of natural oils or cross-metathesis of natural oils with olefins, preferably α-olefins, and particularly ethylene, propylene, 1-butene, 1-hexene, 1-octene, and the like.

As used herein, "monounsaturated" refers to compositions that comprise principally species having a single carbon-carbon double bond but may also include a minor proportion of one or more species that have two or more carbon-carbon double bonds. The skilled person will appreciate that it is not necessary and often impractical to produce a purely "monounsaturated" species, and that mixtures comprising principally (but not exclusively) monounsaturated esters, alcohols, and derivatives are contemplated as within the scope of the invention.

Non-limiting examples of procedures for making mono-unsaturated lower alkyl esters by metathesis are disclosed in WO 2008/048522, the contents of which are incorporated herein by reference. In particular, Examples 8 and 9 of WO 2008/048522 may be employed to produce methyl 9-decenoate and methyl 9-dodecenoate. Suitable procedures also appear in U.S. Pat. Appl. Publ. No. 2011/0113679 and PCT Int. Appl. Nos. WO 2012/061093 and WO 2012/061095, the teachings of which are incorporated herein by reference.

Preferably, at least a portion of the monounsaturated alkyl ester has "$\Delta^9$" unsaturation, i.e., the carbon-carbon double bond in the lower alkyl ester is at the 9-position with respect to the ester carbonyl. In other words, there are preferably seven carbons between the ester carbonyl group and the olefin group at C9 and C10. For the $C_{11}$ to $C_{17}$ esters, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty esters that have $\Delta^9$ unsaturation, e.g., methyl oleate, usually have ~100% cis-isomers.

Although a high proportion of trans-geometry (particularly trans-$\Delta^9$ geometry) may be desirable in the metathesis-derived unsaturated fatty alcohol alkoxylates of the invention, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoue and M. Meier, *Appl. Catal., A* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated ester) imparts different physical properties to unsaturated fatty alcohol alkoxylates, including, for example, modified physical form, melting range, compactability, and other important properties. These differences should allow formulators that use unsaturated fatty alcohol alkoxylates greater latitude or expanded choice as they use them in cleaners, detergents, personal care, agricultural uses, specialty foams, and other end uses.

Monounsaturation can also impart advantages to formulated products (including consumer products) that are often not available with the corresponding saturated fatty alcohol alkoxylates. Because crystallinity is disrupted by the presence of a carbon-carbon double bond, monounsaturated alkoxylates usually have lower viscosities than their saturated analogs. Moreover, the alkoxylates can be concentrated and formulated at higher actives levels—sometimes much higher—than their saturated counterparts. For instance, a saturated alcohol ethoxylate might allow a maximum 30 wt. % actives level to give a flowable liquid, whereas an otherwise similar monounsaturated alcohol ethoxylate could allow the actives level to be as high as 70 or 80 wt. %. Thus, the seemingly minor structural change to a monounsaturated product can enable shipment of more concentrated products, reduce or eliminate the need for special handling equipment, and/or ultimately provide substantial cost savings. The monounsaturated alkoxylates are also more effective as compatibilizers for surfactants or other components in the fully formulated products. For evidence of the advantages of using a monounsaturated fatty alcohol alkoxylate, see the microscopy study results discussed below and summarized in Table 4.

Microscopy reveals that the monounsaturated alkoxylates have isotropic and lamellar phases over a wider range of actives levels compared with their saturated analogs. This attribute can expand formulating latitude for many end-use applications. Thus, in one aspect, the invention is a mono-unsaturated fatty alcohol ethoxylate having at least one isotropic clear phase over an increased actives level range when compared with that of a saturated analog of the monounsaturated fatty alcohol ethoxylate. Preferably, the fatty alcohol ethoxylate comprises isotropic and/or lamellar phases at any actives level from 0 to 100%. More preferably, the fatty alcohol ethoxylate comprises an isotropic clear phase at any actives level from 0 to 100%.

Suitable metathesis-derived monounsaturated esters derive from carboxylic acids. Preferably, the esters derive from $C_5$-$C_{35}$ carboxylic acids, more preferably from $C_{10}$-$C_{17}$ carboxylic acids. Example include esters derived from 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like.

Usually, cross-metathesis or self-metathesis of the natural oil is followed by separation of an olefin stream from a modified oil stream, typically by stripping or distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{10}$ alkyl esters, which are essentially spectators in the metathesis reaction. The rest of the product mixture depends on whether cross- or self-metathesis is used. When the natural oil is cross-metathesized with an α-olefin and the product mixture is transesterified, the resulting alkyl ester mixture includes a $C_{10}$ unsaturated alkyl ester and one or more $C_{11}$ to $C_{17}$ unsaturated alkyl ester coproducts in addition to the glycerin by-product. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. The unsaturated alkyl esters are readily separated from each other and easily purified by fractional distillation. These lower alkyl esters are excellent starting materials for making the inventive unsaturated alcohol alkoxylate compositions.

Natural oils suitable for use as a feedstock to generate the monounsaturated alkyl esters from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, linseed oil, tung oil, jatropha oil, mustard oil, pennycress oil, camellina oil, tallow, lard, poultry fat, fish oil, and the like. Soybean oil, palm oil, rapeseed oil, and mixtures thereof are preferred natural oils.

Oils produced using bioengineered microorganisms can be used as feedstocks. Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty groups derived from oleic acid. Thus, particularly preferred natural oils include soybean oil, palm oil, algal oil, and rapeseed oil.

A modified natural oil, such as a partially hydrogenated vegetable oil or an oil modified by a fermentation process, can be used instead of or in combination with the natural oil. When a natural oil is partially hydrogenated or modified by fermentation, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to inventive unsaturated alcohol derivative compositions. In certain embodiments, the naturally occurring oil may be refined, bleached, and/or deodorized.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

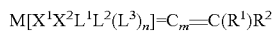

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^3$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ-with respect to the carbene carbon to provide the bidentate ligand. Examples of suitable Grubbs-Hoveyda catalysts appear in the '086 publication.

The structures below provide just a few illustrations of suitable catalysts that may be used:

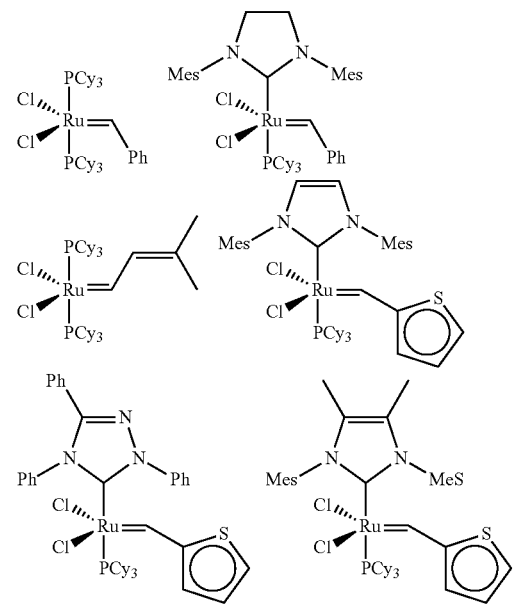

Heterogeneous catalysts suitable for use in the self- or cross-metathesis reaction include certain rhenium and molybdenum compounds as described, e.g., by J. C. Mol in *Green Chem.* 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein. See also *J. Org. Chem.* 46 (1981) 1821; *J. Catal.* 30 (1973) 118; *Appl. Catal.* 70 (1991) 295;

*Organometallics* 13 (1994) 635; *Olefin Metathesis and Metathesis Polymerization* by Ivin and Mol (1997), and *Chem. & Eng. News* 80(51), Dec. 23, 2002, p. 29, which also disclose useful metathesis catalysts. Illustrative examples of suitable catalysts include ruthenium and osmium carbene catalysts as disclosed in U.S. Pat. Nos. 5,312,940, 5,342,909, 5,710,298, 5,728,785, 5,728,917, 5,750,815, 5,831,108, 5,922,863, 6,306,988, 6,414,097, 6,696,597, 6,794,534, 7,102,047, 7,378,528, and U.S. Pat. Appl. Publ. No. 2009/0264672 A1, and PCT/US2008/009635, pp. 18-47, all of which are incorporated herein by reference. A number of metathesis catalysts that may be advantageously employed in metathesis reactions are manufactured and sold by Materia, Inc. (Pasadena, Calif.) and Evonik Degussa GmbH (Hanau, Germany).

The unsaturated fatty alcohols (also referred to hereinbelow as simply "unsaturated alcohols") are made by reacting a metathesis-derived monounsaturated alkyl ester, preferably a $C_5$-$C_{35}$ monounsaturated alkyl ester, and more preferably a $C_{10}$-$C_{17}$ monounsaturated lower alkyl ester, with a reducing agent. By "lower alkyl ester," we mean an ester derived from a $C_1$ to $C_{10}$ alcohol, preferably a $C_1$-$C_6$ alcohol, more preferably a $C_1$-$C_4$ alcohol, and most preferably methanol or ethanol. Thus, the lower alkyl ester is most preferably a methyl or ethyl ester. Suitable lower alkyl esters can be generated by transesterifying a metathesis-derived triglyceride. For example, cross-metathesis of a natural oil with an olefin, followed by removal of unsaturated hydrocarbon metathesis products by stripping, and then transesterification of the modified oil component with a lower alkanol under basic conditions provides a mixture of unsaturated lower alkyl esters. The unsaturated lower alkyl ester mixture can be purified to isolate particular alkyl esters prior to making the unsaturated alcohols and inventive alkoxylates.

Reduction of metathesis-derived monounsaturated alkyl esters to produce the unsaturated alcohols is performed using well-known catalysts and procedures. The reducing agent is typically either a hydride reducing agent (sodium borohydride, lithium aluminum hydride, or the like) or molecular hydrogen in combination with a metal catalyst, frequently copper and/or zinc in combination with chromium (see, e.g., U.S. Pat. Nos. 2,865,968; 3,193,586; 4,804,790; 5,124,491; 5,672,781; 6,683,224; 7,169,959 and 7,208,643, the teachings of which are incorporated herein by reference).

The skilled person will appreciate that the reduction process, particularly when transition metal catalysts are used to convert the lower alkyl esters to alcohols, can induce some degree of isomerization or migration of the carbon-carbon double bond from its original position. Moreover, because ester hydrogenation catalysts are not always completely selective, a proportion of the carbon-carbon double bonds might be hydrogenated during the ester reduction, resulting in a mixed product that may have saturated fatty alcohols in addition to the desired unsaturated fatty alcohols. The skilled person can control the degree of unsaturation to any desired amount.

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. Structures shown often refer to a principal product that may be accompanied by a lesser proportion of other components or positional isomers. Thus, the structures provided represent likely or predominant products.

Some monounsaturated fatty alcohol compositions used to make the inventive alkoxylates have the general structure:

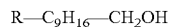

wherein R is H or $C_2$-$C_7$ alkyl. Preferably, the fatty alcohol compositions have the general structure:

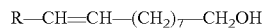

wherein R is H or $C_2$-$C_7$ alkyl.

Some specific examples of $C_{10}$, $C_{12}$, $C_{14}$, and $C_{16}$-based unsaturated alcohols used to make inventive alkoxylates appear below:

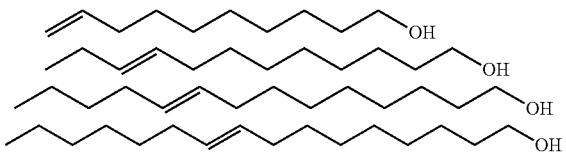

The inventive alkoxylates are made by alkoxylating the monounsaturated fatty alcohol compositions.

The unsaturated fatty alcohols can be alkoxylated using well-known techniques. For instance, the unsaturated fatty alcohol can be alkoxylated by reacting it with ethylene oxide, propylene oxide, or a combination thereof to produce an alkoxylate. Alkoxylations are usually catalyzed by a base (e.g., KOH), but other catalysts such as double metal cyanide complexes (see, e.g., U.S. Pat. No. 5,482,908) can also be used. The oxyalkylene units can be incorporated randomly or in blocks. Preferably, the fatty alcohol is ethoxylated with ethylene oxide.

Some specific examples of ethoxylates based on $C_{10}$, $C_{12}$, $C_{14}$, and $C_{16}$ unsaturated alcohols appear below:

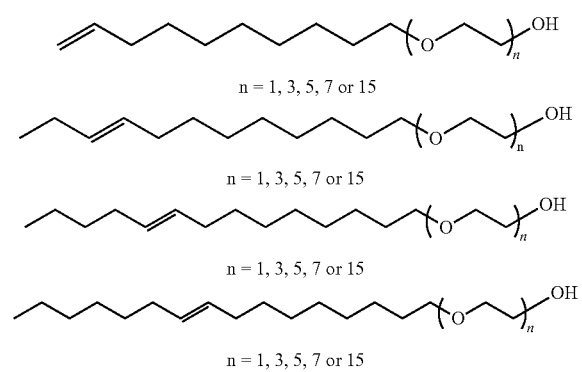

In one aspect, a monounsaturated alkoxylate is made by reacting a monounsaturated alcohol (or alkoxide) with one or more alkylene oxides. As shown in the examples below, a series of products with different degrees of alkoxylation can be easily produced using a single reactor. This is illustrated by the sequential ethoxylation of 9-decen-1-ol or 9-dodecen-1-ol to produce ethoxylates having, on average, 1, 3, 5, 7, or 15 moles of oxyethylene units per mole of unsaturated fatty alcohol starter. (See, e.g., the preparation of ethoxylates from 9-decen-1-ol: A10-4, A10-7, A10-10, A10-13, and A10-16).

Thus, in one aspect, the alkoxylate of the monounsaturated alcohol composition has the general structure:

wherein R is H or $C_2$-$C_7$ alkyl; AO is an oxyalkylene group, preferably oxyethylene; and n, which is the average number of oxyalkylene groups, has a value within the range of 0.1 to 200, preferably 0.5 to 100. Preferably, n has a value within the range of 1 to 50, more preferably 1 to 20. Preferably, the derivative has the general structure:

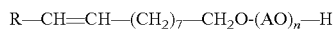

wherein R is H or $C_2$-$C_7$ alkyl; AO is an oxyalkylene group, preferably oxyethylene; and n, which is the average number of oxyalkylene groups, has a value within the range of 0.1 to 200, preferably 0.5 to 100. Preferably, n has a value within the range of 1 to 50, more preferably 1 to 20.

In either of the above-mentioned general structures, AO can indicate a single kind of oxyalkylene group, blocks of different oxyalkylene groups, a random distribution of oxyalkylene groups (as in a random EO/PO copolymer), or any other distribution of oxyalkylene groups. Preferably, AO is oxyethylene.

The invention includes a process for making alkoxylates. The process comprises first reducing a metathesis-derived monounsaturated alkyl ester, preferably a $C_5$-$C_{35}$ monounsaturated alkyl ester, and more preferably a $C_{10}$-$C_{17}$ monounsaturated lower alkyl ester, to produce a monounsaturated fatty alcohol composition. The fatty alcohol composition is then converted to an alkoxylate. Suitable reagents and processes for effecting the reduction have already been described. The process comprises alkoxylating the fatty alcohol composition with one or more alkylene oxides to give a monounsaturated alkoxylate.

The invention provides compositions comprising at least one unsaturated fatty alcohol alkoxylate. The composition may be an aqueous system or provided in other forms. The unsaturated fatty alcohol alkoxylates may be incorporated into various formulations and used as surfactants, emulsifiers, skin feel agents, film formers, rheological modifiers, solvents, release agents, biocides, biocide potentiators, conditioners, dispersants, hydrotropes, or the like. Such formulations may be used in end-use applications including, among others: personal care; household, industrial, and institutional cleaning products; oil field applications; enhanced oil recovery; gypsum foamers; coatings, adhesives and sealants; and agricultural formulations.

Thus, the unsaturated fatty alcohol alkoxylates may be used in such personal care applications as bar soaps, bubble baths, liquid cleansing products, conditioning bars, oral care products, shampoos, body washes, facial cleansers, hand soaps/washes, shower gels, wipes, baby cleansing products, creams/lotions, hair treatment products, antiperspirants, and deodorants.

Cleaning applications include, among others, household cleaners, degreasers, sanitizers and disinfectants, liquid and powdered laundry detergents, heavy duty liquid detergents, light-duty liquid detergents, hard and soft surface cleaners for household, autodish detergents, rinse aids, laundry additives, carpet cleaners, spot treatments, softergents, liquid and sheet fabric softeners, industrial and institutional cleaners and degreasers, oven cleaners, car washes, transportation cleaners, drain cleaners, industrial cleaners, foamers, defoamers, institutional cleaners, janitorial cleaners, glass cleaners, graffiti removers, concrete cleaners, metal/machine parts cleaners, and food service cleaners.

In specialty foam applications (firefighting, gypsum, concrete, cement wallboard), the alkoxylates and derivatives function as foamers, wetting agents, and foam control agents.

In paints and coatings, the alkoxylates are used as solvents, coalescing agents, surfactants, or additives for emulsion polymerization.

In oil field applications, the alkoxylates can be used for oil and gas transport, production, stimulation, enhanced oil recovery, and as components of drilling fluids.

In agricultural applications, the alkoxylates are used as solvents, dispersants, surfactants, emulsifiers, wetting agents, formulation inerts, or adjuvants. As demonstrated in the examples below, the inventive alkoxylates are exceptionally useful as solvents and as nonionic emulsifiers for agricultural compositions.

The following examples merely illustrate the invention. The skilled person will recognize many variations that are within the spirit of the invention and scope of the claims.

Reduction of Methyl 9-Decenoate to 9-Decen-1-ol (A10-1)

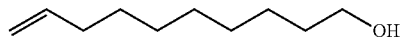

The procedure of Micovic and Mihailovic (*J. Org. Chem.* 18 (1953) 1190) is generally followed. Thus, a 5-L flask equipped with a mechanical stirrer, thermocouple, addition funnel, and nitrogen inlet is charged with tetrahydrofuran ("THF," 3 L). The flask is immersed in an isopropanol/$CO_2$ bath. Lithium aluminum anhydride (LAH) pellets (133.8 g) are charged to the flask with stirring. Methyl 9-decenoate (250 g) is charged to the addition funnel and diluted with THF to the maximum capacity of the funnel (500 mL). The ester solution is added dropwise to the LAH suspension at a rate that maintains the reaction temperature below 20° C. The funnel is refilled with pure ester (750 g; total of 1000 g) due to the large volume of the reaction mixture, and the addition continues. Total addition time of the ester: 5 h. Once the addition is complete, the reaction temperature is ~15° C. and stirring continues for 30 min. $^1$H NMR analysis shows complete conversion of the ester to the desired alcohol.

Deionized water (135 g) is added slowly via the addition funnel while keeping the temperature below 20° C. Hydrogen evolution appears to cease after approximately half of the water is added. The viscosity of the mixture increases, but it remains stirrable. The flask is removed from the cooling bath, and aqueous sodium hydroxide (15% aq. NaOH, 135 g) is added. During this addition, the reaction mixture thickens and quickly becomes an unstirrable slurry that has to be broken up with a spatula. Addition of the remaining NaOH solution proceeds without incident. Following the 15% NaOH addition, deionized water (3×135 g) is added. The slurry stirs for 20 min. and then stands overnight at room temperature. The mixture is filtered through a Buchner funnel, and the filter cake is washed with additional THF (2×500 mL) and then acetone (2×500 mL). The filtrates are combined and concentrated. $^1$H NMR analysis of the remaining oil reveals a clean alcohol product. The crude alcohol is transferred to a round-bottom flask and heated to 50° C. Full vacuum is slowly applied to remove low-boiling volatiles. The remaining crude product is then vacuum distilled, collecting the product that boils at 95-98°

C. (97.5-100° C. pot temperature). Yield of A10-1: 834.7 g (98.3%). Purity (by GC analysis): 99.7%. Hydroxyl value: 355.5 mg KOH/g sample; iodine value: 162.2 g I$_2$/100 g sample. $^1$H NMR (δ, CDCl$_3$): 5.8 (CH$_2$=CH—); 4.95 (CH$_2$=CH—); 3.6 (—CH$_2$—OH). The procedure is repeated four times using 1 kg of ester in each reduction.

Reduction of Methyl 9-Dodecenoate to 9-Dodecen-1-ol (A12-1)

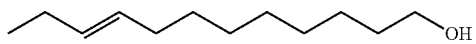

The procedure used to prepare A10-1 is generally followed using THF (3 L), lithium aluminum hydride pellets (116 g), and methyl 9-dodecenoate (1000 g total).

The usual work-up follows, first with deionized water (120 g), then aqueous sodium hydroxide (15% aq. NaOH, 120 g). Following the 15% NaOH addition, deionized water (360 g) is added. The slurry stirs for 20 min. and then stands overnight at room temperature. The mixture is filtered through a Buchner funnel, and the filter cake is washed with additional THF (4×1 L). The filtrates are combined and concentrated.

The procedure is repeated five times using 1 kg of methyl 9-dodecenoate for each run, and the crude alcohol products are combined and distilled as described above for the preparation of A10-1. Yield of A12-1: 4262.8 g (98.2%). Purity (by GC analysis): 99.4%. Hydroxyl value: 302.8 mg KOH/g sample; iodine value: 133.2 g I$_2$/100 g sample. $^1$H NMR (δ, CDCl$_3$): 5.4 (—CH=CH—); 3.6 (—CH$_2$—OH); 0.9 (CH$_3$—).

Additional samples of 9-dodecen-1-ol are produced by reducing methyl 9-dodecenoate using a Zn—Cr catalyst in fixed-bed process. The product gives satisfactory analytical data.

Ethoxylation of 9-Decen-1-ol to Produce 1, 3, 5, 7, and 15 Mole Alcohol Ethoxylates (A10-4, A10-7, A10-10, A10-13, and A10-16, Respectively)

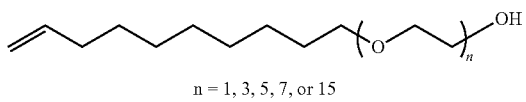

n = 1, 3, 5, 7, or 15

Ethoxylations are performed sequentially using one reactor to prepare unsaturated alcohol ethoxylates from 9-decen-1-ol that have, on average, 1, 3, 5, 7, or 15 oxyethylene units.

9-Decen-1-ol (3417.8 g) is charged to a 2.5-L pressure reactor. Liquid KOH (45%, 45.0 g) is added. The reactor is sealed and heated to 75° C. under nitrogen with agitation. At ~75° C., vacuum is applied to remove water. The contents are further heated to 105-115° C. under full vacuum and held for 4 h with a nitrogen sparge. Vacuum is released, and a removed sample has a water content of 0.04%.

The remaining dried catalyzed alcohol feed (3332.0 g) is heated to 145° C. The reactor is pressurized with nitrogen and vented three times. Ethylene oxide (925 g, 1 mole per mole of starter) is introduced to the reactor at 145-160° C. After the EO addition, the mixture digests for 1 h at 150-160° C. until the reactor pressure equilibrates. The mixture is cooled to 60° C. and partially drained (1175.0 g removed) to provide the 1 mole ethoxylated unsaturated alcohol, A10-4. Hydroxyl value: 281.3 mg KOH/g; iodine value: 125.4 g I$_2$/100 g sample; polyethylene glycol: 0.13%. $^1$H NMR (δ, d$_4$-MeOH): 5.8 (CH$_2$=CH—); 4.9 (CH$_2$=CH—); 3.65-3.45 (—CH$_2$—CH$_2$—OH).

The reactor contents (3082.0 g) are re-heated to 150° C., and the reactor is vented with nitrogen as described earlier. Ethylene oxide (1340.0 g, 2 additional moles per mole of starter; 3 moles of EO per mole of 9-decen-1-ol charged) is added to the feed at 145-160° C. After digesting 1 h at 150-160° C., the mixture is cooled to 60° C. and partially drained (1233.3 g removed) to recover the 3 mole ethoxylated unsaturated alcohol, A10-7. Hydroxyl value: 194.2 mg KOH/g; iodine value: 86.5 g I$_2$/100 g sample; polyethylene glycol: 0.24%. $^1$H NMR (δ, d$_4$-MeOH): 5.8 (CH$_2$=CH—); 4.9 (CH$_2$=CH—); 3.65-3.45 (—CH$_2$—CH$_2$—O—).

The reactor contents (3188.7 g) are re-heated to 150° C. as described above. Ethylene oxide (970 g, 2 additional moles per mole of starter; 5 moles of EO per mole of 9-decen-1-ol charged) is added to the feed at 145-160° C. After digesting 1 h at 150-160° C., the mixture is cooled to 60° C. and partially drained (1277.8 g removed) to recover the 5 mole ethoxylated unsaturated alcohol, A10-10. Hydroxyl value: 146.5 mg KOH/g; iodine value: 65.8 g I$_2$/100 g sample; polyethylene glycol: 0.29%. $^1$H NMR (δ, d$_4$-MeOH): 5.8 (CH$_2$=CH—); 4.9 (CH$_2$=CH—); 3.65-3.45 (—CH$_2$—CH$_2$—O—).

The reactor contents (2880.8 g) are re-heated to 150° C. as described above. Ethylene oxide (670 g, 2 additional moles per mole of starter; 7 moles of EO per mole of 9-decen-1-ol charged) is added to the feed at 145-160° C. After digesting 1 h at 150-160° C., the mixture is cooled to 60° C. and partially drained (1301.1 g removed) to recover the 7 mole ethoxylated unsaturated alcohol, A10-13. Hydroxyl value: 118.5 mg KOH/g; iodine value: 53.0 g I$_2$/100 g sample; polyethylene glycol: 0.27%. $^1$H NMR (δ, d$_4$-MeOH): 5.8 (CH$_2$=CH—); 4.9 (CH$_2$=CH—); 3.65-3.45 (—CH$_2$—CH$_2$—O—).

The reactor contents (2249.7 g) are re-heated to 150° C. Ethylene oxide (1695 g, 8 additional moles per mole of starter; 15 moles of EO per mole of 9-decen-1-ol charged) is added at 145-160° C. After digesting 1 h at 150-160° C., the mixture is cooled to 60° C. and drained to provide the 15 mole ethoxylated unsaturated alcohol, A10-16 (3944.8 g). Hydroxyl value: 67.8 mg KOH/g; iodine value: 30.1 g I$_2$/100 g sample; polyethylene glycol: 1.18%. $^1$H NMR (δ, d$_4$-MeOH): 5.8 (CH$_2$=CH—); 4.9 (CH$_2$=CH—); 3.65-3.45 (—CH$_2$—CH$_2$—O—).

Ethoxylation of 9-Dodecen-1-ol to Produce 1, 3, 5, 7, and 15 Mole Alcohol Ethoxylates (A12-4, A12-7, A12-10, A12-13, and A12-16, Respectively)

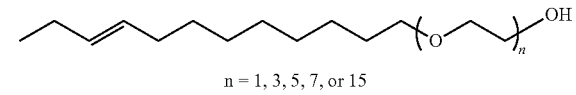

n = 1, 3, 5, 7, or 15

Ethoxylations are performed sequentially using one reactor to prepare unsaturated alcohol ethoxylates from 9-dodecen-1-ol that have, on average, 1, 3, 5, 7, or 15 oxyethylene units.

The procedure used to make the corresponding products from 9-decen-1-ol is generally followed. Thus, 9-dodecen-1-ol (3682.6 g) is charged to a 2.5-L pressure reactor. Liquid KOH (45%, 34.0 g) is added. The reactor is sealed and heated to 100° C. under nitrogen with agitation. At ~100° C., vacuum is applied to remove water. The contents are further heated to 115° C. under full vacuum and held for 3 h with a nitrogen sparge. Vacuum is released, and a removed sample has a water content of 0.03%.

The remaining dried catalyzed alcohol feed (3584.5 g) is heated to 145° C. The reactor is pressurized with nitrogen and vented three times. Ethylene oxide (850 g, 1 mole per mole of starter) is introduced to the reactor at 145-160° C. After the EO addition, the mixture digests for 1 h at 150-160° C. until the reactor pressure equilibrates. The mixture is cooled to 60° C. and partially drained (1167.0 g removed) to provide the 1 mole ethoxylated unsaturated alcohol, A12-4. Hydroxyl value: 246.4 mg KOH/g; iodine value: 106.8 g I$_2$/100 g sample; polyethylene glycol: 0.26%. $^1$H NMR (δ, CDCl$_3$): 5.3 (—CH=CH—); 3.7-3.4 (—CH$_2$—CH$_2$—O—); 0.9 (CH$_3$—).

The reactor contents (3267.8 g) are re-heated to 150° C., and the reactor is vented with nitrogen as described earlier. Ethylene oxide (1250 g, 2 additional moles per mole of starter; 3 moles of EO per mole of 9-dodecen-1-ol charged) is added to the feed at 145-160° C. After digesting 1 h at 150-160° C., the mixture is cooled to 60° C. and partially drained (1219.8 g removed) to recover the 3 mole ethoxylated unsaturated alcohol, A12-7. Hydroxyl value: 177.4 mg KOH/g; iodine value: 76.8 g I$_2$/100 g sample; polyethylene glycol: 0.57%. $^1$H NMR (δ, CDCl$_3$): 5.3 (—CH=CH—); 3.7-3.4 (—CH$_2$—CH$_2$—O—); 0.9 (CH$_3$—).

The reactor contents (3298.0 g) are re-heated to 150° C. as described above. Ethylene oxide (915 g, 2 additional moles per mole of starter; 5 moles of EO per mole of 9-dodecen-1-ol charged) is added to the feed at 145-160° C. After digesting 1 h at 150-160° C., the mixture is cooled to 60° C. and partially drained (1170.9 g removed) to recover the 5 mole ethoxylated unsaturated alcohol, A12-10. Hydroxyl value: 137.4 mg KOH/g; iodine value: 59.7 g I$_2$/100 g sample; polyethylene glycol: 0.42%. $^1$H NMR (δ, d$_4$-MeOH): 5.4 (—CH=CH—); 3.7-3.4 (—CH$_2$—CH$_2$—O—); 0.95 (CH$_3$—).

The reactor contents (3042.1 g) are re-heated to 150° C. as described above. Ethylene oxide (660 g, 2 additional moles per mole of starter; 7 moles of EO per mole of 9-dodecen-1-ol charged) is added to the feed at 145-160° C. After digesting 1 h at 150-160° C., the mixture is cooled to 60° C. and partially drained (1547.0 g removed) to recover the 7 mole ethoxylated unsaturated alcohol, A12-13. Hydroxyl value: 112.5 mg KOH/g; iodine value: 48.5 g I$_2$/100 g sample; polyethylene glycol: 0.44%. $^1$H NMR (δ, d$_4$-MeOH): 5.4 (—CH=CH—); 3.7-3.4 (—CH$_2$—CH$_2$—O—); 0.95 (CH$_3$—).

The reactor contents (2155.1 g) are re-heated to 150° C. Ethylene oxide (1535 g, 8 additional moles per mole of starter; 15 moles of EO per mole of 9-dodecen-1-ol charged) is added at 145-160° C. After digesting 1 h at 150-160° C., the mixture is cooled to 60° C. and drained to provide the 15 mole ethoxylated unsaturated alcohol, A12-16 (3680.5 g). Hydroxyl value: 63.3 mg KOH/g; iodine value: 27.7 g I$_2$/100 g sample; polyethylene glycol: 1.2%. $^1$H NMR (δ, d$_4$-MeOH): 5.4 (—CH=CH—); 3.7-3.4 (—CH$_2$—CH$_2$—O—); 0.95 (CH$_3$—).

The ethoxylation procedure used to make A12-13 is generally followed using 9-tetradecen-1-ol to produce A14-8, a C14 alcohol (7 EO) ethoxylate:

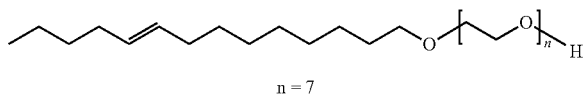

n = 7

A similar ethoxylation strategy is used to prepare A12-21, a C12 alcohol (9 EO) ethoxylate, and A12-22, a C12 alcohol (30 EO) ethoxylate, from 9-dodecen-1-ol.

Agricultural Products: Nonionic Emulsifiers

Nonionic samples contain a low amount of water (<1%) and are prepared as emulsifiable concentrates with three pesticides using two different solvent systems. In the aromatic solvent series, the nonionic sample replaces Toximul® 8240 (castor oil ethoxylate, 36 POE, Stepan), and in the Hallcomid™ (N,N-dimethylcaprylamide/N,N-dimethylcapramide, Stepan) solvent series, the nonionic sample replaces Ninex® MT-630F. The amounts prepared are enough to test two water hardnesses (34 ppm and 1000 ppm) for each of the three samples.

Aromatic Solvent Series.

Sample preparation: Ninate® 60E (calcium alkylbenzenesulfonate, Stepan) and the test sample are stirred until homogeneous. If needed, the nonionic surfactant is melted in an oven at 50-60° C. prior to its combination with Ninate 60E. Controls 1-3 are made by using Toximul 8240 in the amounts indicated instead of the nonionic sample.

Formulations:
1. Bifenthrin, 240 g/L (2.99 g), Aromatic 100 (ExxonMobil, 8.05 g), Ninate 60E (0.38 g), and nonionic sample or Toximul 8240 (0.58 g).
2. 2,4-D ester, 480 g/L (8.90 g), Exxsol® D-110 (ExxonMobil, 2.50 g), Ninate 60E (0.36 g), and nonionic sample or Toximul 8240 (0.24 g).
3. Tebuconazole, 360 g/L (4.45 g), N-methyl-2-pyrrolidone (6.35 g), Ninate 60E (0.48 g), nonionic sample or Toximul 8240 (0.72 g).

Hallcomid Solvent Series.

Sample preparation: The surfactants are combined and stirred until homogeneous, with the nonionic sample melted if needed prior to combination. Controls 1-3 are made by using Ninex MT-630F in the amounts indicated instead of the nonionic sample.

Formulations:
1. Bifenthrin, 240 g/L (2.99 g), Hallcomid M-8-10 (8.29 g), Ninate 60E (0.09 g), Toximul 8320 (0.22 g), Toximul 8242 (0.29 g), and nonionic sample or Ninex MT-630F (0.13 g).
2. 2,4-D diester, 480 g/L (8.90 g), Hallcomid M-8-10 (2.38 g), Ninate 60E (0.09 g), Toximul 8320 (0.22 g), Toximul 8242 (0.29 g), and nonionic sample or Ninex MT-630F (0.13 g).
3. Tebuconazole, 360 g/L (4.45 g), Hallcomid M-8-10 (6.83 g), Ninate 60E (0.09 g), Toximul 8320 (0.22 g), Toximul 8242 (0.29 g), and nonionic sample or Ninex MT-630F (0.13 g).

Emulsion Stability Testing

ASTM E1116-98 (2008) is modified as follows. Flat-bottomed, 100-mL graduated cylinders are charged with 34 ppm or 1000 ppm water (95 mL). A Mohr pipette is used to feed pesticide/surfactant concentrates to each cylinder. Cylinders are stoppered and inverted ten times, then allowed to stand for 0.5, 1, and 24 h while recording stability at each time as type and % separation.

Spontaneity is recorded according to the following criteria: (1) poor: very thin emulsion cloud with major separation of oil droplets; (2) fair: thin emulsion cloud with minor separation of oil droplets; (3) good: thin emulsion cloud reaches the bottom of the cylinder without separation of any type.

Results with both solvent systems are provided in Tables 1A, 1B, 2A, and 2B. Each sample reported in the tables is rated "good" overall as a nonionic surfactant.

TABLE 1A

Performance as a Nonionic Surfactant: Aromatic Solvents

|  |  | 34 ppm water | | | 1000 ppm water | | |
|---|---|---|---|---|---|---|---|
|  | pesticide | Spon. | 1 h | 24 h | Spon. | 1 h | 24 h |
| Control 1 | Bifenthrin | G | 2.5 C | 3 C, 1 CO, 1 O | G | 2 C | 2 C, 1 CO, 1 O |
|  | 2,4-D | F | 2.5 O | 5 O | F | 4.8 O | 5 O |
|  | Tebucon. | F | 1.6 C | 3 C, 2 OC | G | 1.8 C | 1.5 C, 2.5 OC |
| A10-4 | Bifenthrin | P | 7.5 CO | 3 O, 3 OC | P | 6 O | 6 O |
|  | 2,4-D | P | 4.5 CO | 2 O, 1 CO, 2 C | P | 3.8 O | 4 O |
|  | Tebucon. | P | 2 GC | 3 GC | P | 3 GC | 4 GC |
| A10-7 | Bifenthrin | P | 7 CO | 6.5 CO | P | 6 O | 5 O |
|  | 2,4-D | P | 4 CO | 1 O, 4.5 CO | P | 4 O | 4 O |
|  | Tebucon. | P | 2 GC | 3 GC | P | 2.5 GC | 3 GC |
| A10-10 | Bifenthrin | F | NS | 3.5 C | F | 3 O, 5 CO | 4.5 O, 1 CO |
|  | 2,4-D | F | 1.5 CO | 4.1 C | P | 4 CO | 1 O, 4 CO |
|  | Tebucon. | P | 2 CO | 2.5 CO | P | 2.5 CO | 3 CO |
| A10-13 | Bifenthrin | F | 3 C | 5.8 C | G | NS | 2.6 O |
|  | 2,4-D | G | 2.8 C | 4.6 C | F | 3.9 CO | 1 O, 4 CO |
|  | Tebucon. | P | 1.5 CO, 0.5 C | 2.8 CO | P | 2.1 CO | 3.5 CO |
| A10-16 | Bifenthrin | P | 7 C | 7 C | P | 6 C | 4.8 CO |
|  | 2,4-D | P | 2.6 C | 5 C | P | 2.8 C | 3.9 C |
|  | Tebucon. | P | 1 C | 3.5 CO | P | 1.2 C | 2 CO |

Spontaneity: G = good; F = fair; P = poor. Appearance: C = creamy; CO = creamy oil; O = oil; GC = gritty cream; NS = no separation; OC = oily cream.
Numbers are amounts in mL.
Control 1 replaces test sample with Toximul 8240 (castor oil ethoxylate).

TABLE 1B

Performance as a Nonionic Surfactant: Aromatic Solvents (cont.)

|  |  | 34 ppm water | | | 1000 ppm water | | |
|---|---|---|---|---|---|---|---|
|  | pesticide | Spon. | 1 h | 24 h | Spon. | 1 h | 24 h |
| Control 1 | Bifenthrin | G | 2.5 C | 3 C, 1 CO, 1 O | G | 2 C | 2 C, 1 CO, 1 O |
|  | 2,4-D | F | 2.5 O | 5 O | F | 4.8 O | 5 O |
|  | Tebucon. | F | 1.6 C | 3 C, 2 OC | G | 1.8 C | 1.5 C, 2.5 OC |
| A12-4 | Bifenthrin | P | 8 C | 4 O, 1 C | P | 5.2 O | 5.2 O |
|  | 2,4-D | P | 6 C | 6.7 C | P | 4.7 O | 4.5 O |
|  | Tebucon. | P | 2.3 C | 2.5 GC | P | 2.3 C | 2.7 GC |
| A12-7 | Bifenthrin | P | 8.8 C | 6.8 C | P | 4.5 O | 4.9 O |
|  | 2,4-D | P | 3.2 C | 5.5 C | P | 4.2 O | 0.8 O, 3.3 CO |
|  | Tebucon. | P | 2.3 C | 3 GC | P | 2.6 C | 3.2 GC |
| A12-10 | Bifenthrin | F | 2.3 C | 9 C | F | 3 O, 4.1 C | 4 O, 3 C |
|  | 2,4-D | F | 0.7 C | 3.9 C | P | 4.6 CO | 0.75 O, 4.3 CO |
|  | Tebucon. | P | 2.6 C | 4 GC | P | 2.1 C | 3.2 GC |
| A12-13 | Bifenthrin | F | 1 C | 4.9 C | G | Tr. C | 0.5 CO, 1 C |
|  | 2,4-D | F | 3.5 C | 5 C | F | 5.2 CO | 5 CO |
|  | Tebucon. | P | 1.8 C | 3 GC, 4 CO | P | 2.4 C | 3.5 GC |
| A12-16 | Bifenthrin | F | 5.9 C | 6 C | P | 5.5 C | 5 C |
|  | 2,4-D | P | 3.9 C | 5.3 C | P | 2.9 C | 4 C |
|  | Tebucon. | F | 1.8 CO | 3 GC | F | 1.9 CO | 3 GC |

Spontaneity: G = good; F = fair; P = poor. Appearance: C = creamy; CO = creamy oil; O = oil; GC = gritty cream; OC = oily cream. Tr. = trace.
Numbers are amounts in mL.
Control 1 replaces test sample with Toximul 8240 (castor oil ethoxylate).

TABLE 2A

Performance as a Nonionic Surfactant: Hallcomid Solvent

|  |  | 34 ppm water | | | 1000 ppm water | | |
|---|---|---|---|---|---|---|---|
|  | pesticide | Spon. | 1 h | 24 h | Spon. | 1 h | 24 h |
| Control 2 | Bifenthrin | G | 6 OC | 6 O | G | 6 OC | 6 O |
|  | 2,4-D | F | 5 C | 9.8 C | F | 5.5 C | 9.5 C |
|  | Tebucon. | G | 1 C | 4 C | G | 1 C | 4 C, 4 CO |

TABLE 2A-continued

Performance as a Nonionic Surfactant: Hallcomid Solvent

| | | | 34 ppm water | | | 1000 ppm water | |
|---|---|---|---|---|---|---|---|
| | pesticide | Spon. | 1 h | 24 h | Spon. | 1 h | 24 h |
| A10-4 | Bifenthrin | F | NS | NS | F | Tr. GC, 12 C | 3.5 O, 3 CO |
| | 2,4-D | F | 6 C | 9.5 C | F | 6.5 C | 8 C |
| | Tebucon. | F | 3 C | 6.5 C | F | 4 C | 5.8 C |
| A10-7 | Bifenthrin | F | NS | NS | P | 10 CO | 3 O, 3 CO |
| | 2,4-D | F | 5.6 C | 10 C | F | 6 C | 7.5 C |
| | Tebucon. | F | 2.5 C | 5 C | F | 3 C | 5 C |
| A10-10 | Bifenthrin | G | NS | NS | F | 6.5 CO | 4 O, 2 CO |
| | 2,4-D | F | 5 C | 9.9 C | F | 6 C | 8 C |
| | Tebucon. | F | 2 C | 5 C | F | 3.5 C | 2 CO, 5 C |
| A10-13 | Bifenthrin | G | NS | NS | F | 6.4 CO | 6 O |
| | 2,4-D | P | 4.5 C | 8.2 C | F | 5 C | 7.8 C |
| | Tebucon. | F | 2.1 C | 4.9 C | F | 3 C | 5.5 C |
| A10-16 | Bifenthrin | G | NS | NS | F | 5.5 CO | 5.4 O |
| | 2,4-D | P | 4.4 C | 8.5 C | P | 4.8 C | 7.6 C |
| | Tebucon. | F | 1 C | NS | F | 2 C | 4.7 C |

Spontaneity: G = good; F = fair; P = poor. Appearance: C = creamy; CO = creamy oil; O = oil; GC = gritty cream; NS = no separation; OC = oily cream. Tr. = trace.
Numbers are amounts in mL.
Control 2 replaces test sample with Ninex MT-630F (fatty acid ethoxylate).

TABLE 2B

Performance as a Nonionic Surfactant: Hallcomid Solvent (cont.)

| | | | 34 ppm water | | | 1000 ppm water | |
|---|---|---|---|---|---|---|---|
| | pesticide | Spon. | 1 h | 24 h | Spon. | 1 h | 24 h |
| Control 2 | Bifenthrin | G | 6 OC | 6 O | G | 6 OC | 6 O |
| | 2,4-D | F | 5 C | 9.8 C | F | 5.5 C | 9.5 C |
| | Tebucon. | G | 1 C | 4 C | G | 1 C | 4 C, 4 CO |
| A12-4 | Bifenthrin | G | NS | NS | F | 11 C | 2 O, 3 CO |
| | 2,4-D | F | 6.2 C | 8.8 C | F | 6.9 C | 8.6 C |
| | Tebucon. | F | 3.1 C | 5.9 C | F | 3.1 C | 6 C |
| A12-7 | Bifenthrin | G | NS | NS | F | 10.2 C | 2 O, 3.5 CO |
| | 2,4-D | F | 6 C | 10 C | F | 6.7 C | 8.2 C |
| | Tebucon. | F | 2 C | 5.1 C | F | 2.7 C | 4.9 C |
| A12-10 | Bifenthrin | G | NS | Tr. C | F | 6.1 O | 3 O, 2 CO |
| | 2,4-D | P | 5.3 C | 9.2 C | F | 6.8 C | 8.7 C |
| | Tebucon. | F | 2.1 C | 5.1 C | F | 2 C | 4.2 C |
| A12-13 | Bifenthrin | G | NS | Tr. C | F | 5.1 CO | 3 O, 2 CO |
| | 2,4-D | P | 4.4 C | 9.6 C | F | 5.2 C | 9 C |
| | Tebucon. | F | 1.3 C | 4.1 C | G | 1.8 C | 4.3 C |
| A12-16 | Bifenthrin | G | NS | NS | F | 6.2 CO | 2 O, 3.6 CO |
| | 2,4-D | P | 4.5 C | 8.5 C | P | 4 C | 7 C |
| | Tebucon. | F | 1.5 C | 3 C | F | 1.5 C | 3 C |

Spontaneity: G = good; F = fair; P = poor. Appearance: C = creamy; CO = creamy oil; O = oil; NS = no separation; OC = oily cream. Tr. = trace.
Numbers are amounts in mL.
Control 2 replaces test sample with Ninex MT-630F (fatty acid ethoxylate).

Agrichemical Solvent Analysis: Active Solubility

Solvency strength of potential agrichemical solvents is evaluated by identifying the solubility level of three standard pesticides in the solvent by weight percent: 2,4-D acid, imidacloprid, and tebuconazole. Testing is performed using a 4-mL vial with a pane magnetic stirrer and an accurately weighed 2 to 2.2-g sample of solvent. The active material is also accurately weighed before addition. Initial amounts of active material are approximately: 2,4-D: 0.3 g; imidacloprid: 0.02 g; tebuconazole: 0.3 g. Solvent and pesticide active are combined, allowed to mix for 1 h at room temperature, and then inspected for the presence of undissolved active material. Additional active material is added in appropriately small increments until it no longer dissolves completely. This mixture is then stirred for 24 h at room temperature, and if the active has completely dissolved, additional active ingredient is added and the mixture is stirred another 24 h at room temperature. The percent solubility is recorded, and performance is compared with that of a standard agricultural solvent.

When the method outlined above is followed, two samples, A10-7 and A10-10, perform as well as the control in this test. See Table 3:

TABLE 3

Agricultural Solvent Testing

| Solvent | 2,4-D Acid | Imidacloprid | Tebuconazole |
|---|---|---|---|
| A10-7 (3 EO) | 29.5 | 2.9 | 13.5 |
| A10-10 (5 EO) | 29.8 | 2.8 | 13.0 |
| Methyl caprylate/caprate | 14.8 | 0.4 | 10.9 |
| N,N-dimethylcapramide | 45.4 | 4.2 | 38.8 |

TABLE 3-continued

Agricultural Solvent Testing

| Solvent | 2,4-D Acid | Imidacloprid | Tebuconazole |
|---|---|---|---|
| aromatic hydrocarbon | 0.6 | 1.0 | 4.2 |
| N-methyl-2-pyrrolidone | 39.5 | 29.3 | 62.2 |

Surfactant Phase Behavior Study:

Phase behavior is observed using an Olympus BH-2 cross-polarized microscope at 100-400× and room temperature (20° C. to 22° C.). The inventive monounsaturated alcohol ethoxylates are compared with their saturated analogs.

Samples are prepared by diluting the most concentrated product gradually with deionized water. When the surfactant concentration approaches a phase transition, the concentration is varied at 2-4% intervals to estimate the phase boundary. The actives level reported in Table 4 for each phase boundary is within ±5% of the true boundary.

Samples are loaded between a microscope slide and cover glass and are allowed to equilibrate before observation. Microscopic texture is analyzed and used to determine the phase. For some samples, an AR 2000 rheometer (TA Instruments) is used to measure viscosity at 25° C. to further verify phase behavior.

At low surfactant concentrations, randomly oriented micelles (spheres or cylinders) generally predominate, resulting in a clear or isotropic liquid. As concentration increases, cylindrical micelles can arrange themselves into either hexagonal or cubic phases, both of which have very high viscosities (10-50K cP at 25° C. for the hexagonal phase, higher for the cubic phase). Thus, in the hexagonal and cubic phases, the surfactant is difficult to process or formulate. Increasing the surfactant concentration more can generate a lamellar phase, where micellar bilayers are separated by water. Because the lamellar phase is pumpable (1-15K cP at 25° C.), compositions having high levels of surfactant actives can be produced. Further concentration of the surfactant can lead to reverse micelles, in some cases generating an isotropic mixture. In sum, phase behavior is important for manufacture, processing, transportation, and formulation of compositions containing surfactants.

An ideal sample is isotropic and clear throughout the entire range of active levels with low viscosity, as this is most likely to avoid any processing issues related with gelling or precipitation during formulation. Isotropic opaque, mixed isotropic and lamellar, and lamellar phases are also considered favorable for ease of processing and formulating. Less favorable gel phases include cubic, hexagonal, and paste. The presence of these phases at a particular actives level suggests that processing at or near that actives level will be very difficult, and precipitation of the surfactant may occur when used at or near that actives level.

Results of the microscopy study appear in Table 4. In general, the results demonstrate that the inventive monounsaturated compositions are more likely to have a clear isotropic phase over most or all actives ranges compared with their saturated analogs (see, e.g., A10-10 or A10-13 versus their saturated analogs).

For samples in which the same phases are present, the monounsaturated compositions tend to have a broader actives range for the more favorable phase. See, e.g., A10-7, in which the combined isotropic phases (clear and opaque) are about 50% of the total, with the balance being lamellar; in contrast, the saturated analog has about 38% of the isotropic phases. Similarly, in A12-7, the isotropic portion comprises about 66% of the total, while the saturated analog has about 38% of the isotropic phases.

The monounsaturated compositions are less likely to have the more troublesome gel phases (hexagonal, cubic, and paste); when they are present in the monounsaturated compositions, the ranges tend to be narrower. For instance, A10-16 is isotropic and clear up to about 93% actives, with no cubic component, while its saturated analog exhibits a cubic phase at intermediate actives levels (37-55%); this should translate into a substantial advantage in handling and formulating for the unsaturated composition. A12-13 and its saturated analog both have a hexagonal phase, but A12-13 has more generous isotropic regions (0-35%, 57-100%) and no lamellar component.

In sum, the microscopy study indicates that the inventive monounsaturated compositions will offer compatibility and processing advantages to formulators that use these surfactants, particularly when compared to the saturated analogs.

TABLE 4

Comparison of Monounsaturated Alcohol Ethoxylates v. Saturated Analogs: Estimated Phase Region as a Function of % Actives Level[1]

|  | Isotropic Clear | Isotropic Opaque | Lamellar/ Isotropic | Lamellar | Hexagonal | Cubic | Paste |
|---|---|---|---|---|---|---|---|
| A10-7 (3 EO) | 70-100 | 0-20 |  | 20-70 |  |  |  |
| sat. analog[2] | 90-100 | 0-28 |  | 28-90 |  |  |  |
| A10-10 (5 EO) | 0-100 |  |  |  |  |  |  |
| sat. analog | 0-55, 80-100 |  |  | 55-80 |  |  |  |
| A10-13 (7 EO) | 0-100 |  |  |  |  |  |  |
| sat. analog | 0-43, 60-100 |  |  | 43-60 |  |  |  |
| A10-16 (15 EO) | 0-93 |  |  |  |  |  | 93-100 |
| sat. analog | 0-37, 55-93 |  |  |  |  | 37-55 | 93-100 |
| A12-7 (3 EO) | 74-100 | 0-40 |  | 40-74 |  |  |  |
| sat. analog | 90-100 | 0-28 |  | 28-90 |  |  |  |
| A12-10 (5 EO) | 0-35, 80-100 |  | 35-50 | 50-80 |  |  |  |
| sat. analog | 0-30, 83-100 |  | 30-40 | 40-83 |  |  |  |
| A12-13 (7 EO) | 0-35, 57-100 |  |  |  | 35-57 |  |  |
| sat. analog | 0-30, 90-100 |  |  | 67-90 | 30-67 |  |  |
| A12-16 (15 EO) | 0-30, 57-60, 70-93 |  |  |  | 60-70 | 30-57 | 93-100 |
| sat. analog | 0-28, 73-93 |  |  |  | 50-73 | 28-50 | 93-100 |

[1]All microscopy examinations are performed at room temperature. Phase boundaries are estimates.
[2]Saturated analogs prepared by catalytic hydrogenation.

Hard-Surface Cleaners: Aqueous Degreasers

This test measures the ability of a cleaning product to remove a greasy dirt soil from a white vinyl tile. The test is automated and uses an industry standard Gardner Straight Line Washability Apparatus. A camera and controlled lighting are used to take a live video of the cleaning process. The machine uses a sponge wetted with a known amount of test product. As the machine wipes the sponge across the soiled tile, the video records the result, from which a cleaning percentage can be determined. A total of 10 strokes are made using test formulation diluted 1:32 with water, and cleaning is calculated for each of strokes 1-10 to provide a profile of the cleaning efficiency of the product. The test sample is used as a component of different control formulations depending on whether it anionic, amphoteric, or nonionic.

Nonionic and Amphoteric Test Samples:

A neutral, dilutable all-purpose cleaner is prepared from propylene glycol n-propyl ether (4.0 g), butyl carbitol (4.0 g), sodium citrate (4.0 g), Stepanol® WA-Extra PCK (sodium lauryl sulfate, Stepan, 1.0 g), test sample (0.90 g if 100% active material), and deionized water (to 100.0 g solution). The control sample for nonionic/amphoteric testing replaces the test sample with Bio-Soft® EC-690 (ethoxylated alcohol, nominally 90% active material, Stepan, 1.0 g).

Soil Composition:

Tiles are soiled with a particulate medium (50 mg) and an oil medium (5 drops). The particulate medium is composed of (in parts by weight) hyperhumus (39), paraffin oil (1), used motor oil (1.5), Portland cement (17.7), silica (18), molacca black (1.5), iron oxide (0.3), bandy black clay (18), stearic acid (2), and oleic acid (2). The oil medium is composed of kerosene (12), Stoddard solvent (12), paraffin oil (1), SAE-10 motor oil (1), Crisco® shortening, product of J.M. Smucker Co. (1), olive oil (3), linoleic acid (3), and squalene (3).

Five alcohol ethoxylate samples (A10-16, A12-10, A12-13, A12-16, and A12-21) perform as well as the control in this test (see Tables 5 and 6).

TABLE 5

Control Runs for Gardner Straight Line Washability Test

| | Ave. % clean after 2, 4, 6, 8, or 10 swipes | | | | |
|---|---|---|---|---|---|
| | 2 | 4 | 6 | 8 | 10 |
| Control 11 | 53.0 | 61.0 | 63.6 | 64.6 | 66.2 |
| Control 20 | 65.0 | 70.7 | 72.2 | 73.7 | 74.0 |
| Control 30 | 73.6 | 88.2 | 94.7 | 96.6 | 98.0 |

TABLE 6

Gardner Straight-Line Washability Nonionic Test Samples

| Sample | Con. # | Compound class | Ave. % clean | | | | | Rating |
|---|---|---|---|---|---|---|---|---|
| | | | 2 | 4 | 6 | 8 | 10 | |
| A10-16 | 11 | alcohol 15 EO ethoxylate | 60.2 | 60.2 | 60.2 | 61.2 | 63.2 | equal |
| A12-10 | 30 | alcohol 5 EO ethoxylate | 89.2 | 91.1 | 92.4 | 94.6 | 94.2 | equal |
| A12-13 | 20 | alcohol 7 EO ethoxylate | 60.2 | 65.6 | 67.0 | 68.2 | 68.2 | equal |
| A12-16 | 20 | alcohol 15 EO ethoxylate | 60.2 | 64.4 | 65.8 | 66.7 | 66.7 | equal |
| A12-21 | 30 | alcohol 9 EO ethoxylate | 86.2 | 91.4 | 91.8 | 91.2 | 92.7 | equal |

Fabric Cleaning: Primary Nonionic Surfactant for Bargain Laundry Detergent

This method evaluates the ability of an experimental sample to perform as a primary nonionic surfactant in a bargain laundry detergent formulation that contains neutralized dodecylbenzene sulfonic acid, a non-ionic surfactant (such as an ethoxylated (7 EO) synthetic $C_{12}$-$C_{15}$ alcohol), citric acid, monoethanolamine, triethanolamine, and a preservative. The experimental nonionic sample replaces all of the alcohol ethoxylate in the standard formulation and is tested for its detergency. Laundry detergent formula (46 g) is charged to the laundry machine, followed by soiled/stained fabric swatches that are attached to pillowcases. Wash temperature: 90° F. Rinse: 70° F. The swatches are detached from pillowcases, dried, and ironed.

Swatches are scanned to measure the L*a*b* values, which are used to calculate a soil removal index (SRI) for each type of swatch. Finally, the ΔSRI is calculated, which equals the experimental sample SRI minus the SRI of a pre-determined standard laundry detergent formula (or control). When |ΔSRI|≥1, differences are perceivable to the naked eye. If the value of ΔSRI is greater than or equal to 1, the sample is superior. If ΔSRI is less than or equal to −1, the sample is inferior. If ΔSRI is greater than −1 and less than 1, the sample is considered equal to the standard.

The control bargain laundry detergent is prepared from sodium hydroxide-neutralized dodecylbenzene sulfonic acid (NaLAS, Bio-Soft® S-101, Stepan, 33.9% actives, 41.3 wt. %), Bio-Soft® N25-7 (fatty alcohol ethoxylate, Stepan, 5.00 wt. %), citric acid (50% aq. solution, 1.00 wt. %), monoethanolamine (1.00 wt. %), triethanolamine (1.00 wt. %), and deionized water plus preservative (balance to 100 wt. %). In the experimental example, the Bio-Soft® N25-7 is completely replaced with an equivalent actives amount of the test sample.

The formulation is made by charging 90% of the total amount of water at 50° C., then adding in order, with mixing, citric acid solution, monoethanolamine, triethanolamine, neutralized sulfonic acid, and Bio-Soft® N25-7 or the experimental sample. The pH is adjusted to 9.5 with 25% aq. NaOH solution, and then preservative and the balance of the water are added.

The following standard soiled/stained fabric swatches are used: dust sebum on cotton (DSC); dust sebum on cotton/polyester (DSCP); beef tallow (BT); clay on cotton (CC); clay on cotton/polyester (CCP); grass on cotton (GC); red wine on cotton (RWC); blueberry on cotton (BC); coffee on cotton (COFC); cocoa on cotton (EMPA 112); blood/ink/milk on cotton (EMPA 116); sebum tefo (ST), and make-up on cotton (EMPA 143). At least three of each kind of swatch are used per wash. Swatches are stapled to pillowcases for laundering, and extra pillowcases are included to complete a six-pound load.

The same procedure is used to launder all of the pillowcases/swatches, with care taken to ensure that water temperature, wash time, manner of addition, etc. are held constant for the cold-water wash process. When the cycle is complete, swatches are removed from the pillowcases, dried at low heat on a rack, and pressed briefly with a dry iron.

A Hunter LabScan® XE spectrophotometer is used to determine the $L^*a^*b^*$ values to calculate the SRI for every type of swatch, and the stain removal index (SRI) is calculated as follows:

$$SRI = 100 - \sqrt{(L^*_{clean} - L^*_{washed})^2 + (a^*_{clean} - a^*_{washed})^2 + (b^*_{clean} - b^*_{washed})^2}$$

$$\Delta SRI = SRI_{sample} - SRI_{standard}$$

As shown in Table 7, four test samples (A12-10, A12-13, A12-21, and A14-8) perform as well as the control sample when evaluated as a primary nonionic surfactant.

TABLE 7

Performance as a Primary Nonionic Surfactant in a Bargain Detergent Formulation: |ΔSRI| Values versus Bio-Soft ® N25-7

| | ΔSRI values | | | |
|---|---|---|---|---|
| test sample | A12-10 | A12-13 | A12-21 | A14-8 |
| dust sebum on cotton (DSC) | −1.0 | −0.3 | 0.1 | −0.5 |
| dust sebum on cotton/polyester (DSCP) | −0.8 | −0.4 | 0.6 | −0.2 |
| beef tallow (BT) | 2.9 | 2.6 | 4.5 | 0.3 |
| clay on cotton (CC) | 0.2 | 0.3 | 0.3 | 0.9 |
| clay on cotton/polyester (CCP) | 0.1 | −0.2 | 0.3 | 0.2 |
| grass on cotton (GC) | −1.7 | −1.3 | −1.2 | 0.7 |
| red wine on cotton (RWC) | −0.5 | 0.6 | 0.2 | −0.1 |
| blueberry on cotton (BC) | −0.1 | −0.8 | 0.0 | −0.3 |
| coffee on cotton (COFC) | −0.4 | 0.2 | 0.2 | 0.0 |
| cocoa on cotton (EMPA 112) | 1.8 | −0.3 | 1.0 | −1.3 |
| blood/ink/milk on cotton (EMPA 116) | −0.8 | −0.9 | −0.4 | 0.5 |
| make-up on cotton (EMPA 143) | 0.4 | −0.1 | 0.3 | 0.0 |
| sebum tefo (ST) | −0.6 | — | 0.5 | 0.6 |
| overall rating | good | good | good | good |

Fabric Cleaning: Compaction

This test evaluates the ability of an experimental sample to produce a concentrated laundry detergent. The sample is formulated into surfactant blends having high actives content. Two experimental derivatives, A12-13 and A12-21, are evaluated.

In a first experiment, a three-component surfactant blend is prepared. This blend comprises the experimental sample (30 wt. %), a linear alkylbenzene sulfonate (15 wt. %), and an alkyl ether sulfate (15 wt. %). The appearance and viscosity of the blend are compared with those of similar three-component blends in which a standard alcohol ethoxylate replaces the experimental sample. Results appear in Table 8. As the table illustrates, the surfactant blends containing A12-13 or A12-21 have similar appearance and viscosity to those of the control blends.

In a second experiment, a two-component surfactant blend is prepared in which the experimental sample and a linear alkylbenzene sulfonate are combined at a 1:1 actives ratio, beginning with a high actives blend having a cloudy appearance. Water is gradually added and mixed with the surfactant blend at room temperature. The percent actives at which the surfactant blend becomes clear and homogeneous at room temperature is compared with that of a control blend of a standard alcohol ethoxylate and the linear alkylbenzene sulfonate. Results appear in Table 8. For both A12-13 and A12-21, the actives level at which the blend is clear and homogeneous at room temperature is comparable to that of the standards.

Based on the results with two- and three-component surfactant blends, experimental samples A12-13 and A12-21 are rated as equal to the standards.

TABLE 8

Fabric Cleaning: Evaluation of Compaction

Three-component blends:

| Blend with: | Appearance, 25° C. | Viscosity (cPs) |
|---|---|---|
| A12-13 | cloudy, flowable gel | 5400 |
| A12-21 | cloudy, flowable gel | 5600 |
| alcohol ethoxylate 1 | cloudy, flowable gel | 5200 |
| alcohol ethoxylate 2 | cloudy, flowable gel | 5000 |

Two-component blends:

| Blend with: | % Actives at which blend is clear and homogeneous at 25° C. |
|---|---|
| A12-13 | 41 |
| A12-21 | 51 |
| alcohol ethoxylate 1 | 38 |
| alcohol ethoxylate 2 | 48 |

Overall rating versus controls: A12-13: equal; A12-21: equal.

Solubility Evaluation: Enhanced Oil Recovery (EOR)

Derivatives are evaluated as the main surfactant in control formulations to determine likely solubility performance in an EOR application. Samples are prepared in a 10% stock solution and evaluated at 1 wt. % with a brine concentration of 1% sodium chloride. Replicate experiments are performed at each temperature with each sample. Results appear in Table 9.

TABLE 9

Solubility Evaluation for EOR Applications

| Sample | Temperature (° C.) | Soluble? | Comments |
|---|---|---|---|
| control | 20.7 | no | white, hazy |
| A10-7 | 20.7 | no | white, opaque |

TABLE 9-continued

Solubility Evaluation for EOR Applications

| Sample | Temperature (° C.) | Soluble? | Comments |
|---|---|---|---|
| control | 51.5 | no | white, hazy |
| A10-7 | 51.5 | no | white, opaque |
| control | 56.1 | no | white, hazy |
| A10-7 | 56.1 | no | white, hazy |

Overall performance of A10-7: Equal to control
Control = fatty alcohol ethoxylate Performance as a Foamer or Foam Additive for Specialty Foamer Applications Specialty foamer applications include (among others) gypsum, concrete, and firefighting foams. The tests below evaluate foam stability when the sample is used as the primary foamer and also evaluate the sample's performance as an additive when used as a foam stabilizer, enhancer, or destabilizer.

Particularly for gypsum, for which set-up times are rapid on commercial production lines, a desirable foam additive helps to control the coalescence of the bubble to provide a larger bubble within a prescribed time frame. Preferably, destabilization of the foam occurs at the end of the first minute in the tests below. A10-13 is identified as a "good" performer as a gypsum foam destabilizer in Table 10 because it allows this balance to be struck effectively.

Foam Stability: Drainage Method

Surfactant solutions (0.4 wt. % active material) are prepared by mixing surfactant with 342 ppm hard water. Surfactant solution (100 mL) is carefully transferred to a stainless-steel mixing cup, then mixed at high speed (27K rpm) using a Hamilton Beach mixer for 10 s. The contents are quickly poured into a 100-mL graduated cylinder to the 100-mL mark, and a stopwatch is immediately started. The amount of liquid settling in the cylinder is recorded every 15 s for 4 min. Less liquid drained indicates greater foam stability.

TABLE 10

Evaluation as a Potential Foamer for Gypsum: Liquid Volume (mL) vs. Drain Time (min) in 342 ppm Hard Water

| | Drain time (min) | | | | | | | | Rating |
|---|---|---|---|---|---|---|---|---|---|
| | 0.5 | 1.0 | 1.5 | 2.0 | 2.5 | 3.0 | 3.5 | 4.0 | |
| Control 1 | 0.25 | 0.75 | 2.50 | 3.75 | 5.75 | 7.50 | 9.50 | 11.50 | — |
| Control 2 | 0.50 | 1.50 | 2.00 | 2.75 | 4.00 | 5.00 | 6.25 | 7.50 | — |
| Control 3 | 0.25 | 1.00 | 2.00 | 3.00 | 4.00 | 5.25 | 6.50 | 7.50 | — |
| Foamer A | 0.25 | 1.00 | 2.25 | 3.00 | 4.00 | 5.00 | 6.00 | 7.00 | — |
| A10-13 | 0.50 | 2.25 | 4.00 | 6.00 | 7.50 | 9.50 | 11.50 | 13.25 | good |

Control 1 = lauramine oxide;
Control 2 = cocamidopropyl betaine;
Control 3 = ammonium alkyl ether sulfate Performance as a Paint Additive Formulations:

Titanium dioxide slurry (Dupont Ti-Pure® R746) is charged to a container, followed by deionized water and propylene glycol, and the contents are mixed (500 rpm). Latex (49% solids) and preservative (Acticide® GA, product of Thor) are added. Thickener (Acrysol™ SCT-275, product of Dow, 0.3%) is slowly charged below the liquid surface by syringe. The pH is adjusted to 9.0 using ammonium hydroxide solution. The batch is mixed for 30 min. and then allowed to stand for at least 2 h. The batch is remixed gently, and a portion (240 g) is transferred to a 400-mL beaker. Solvent ($C_{18}$ amide, 0.5% VOC, EPA Method 24, 5 wt. % based on latex solids) and derivative A12-16 (1% active based on latex solids) are added and mixed at 650 rpm. Viscosity is adjusted to an initial KU of 90 with more thickener. The paint is covered and final KU is measured after 24 h. Its value falls within the range of 93-100 KU and varies from the original measurement by no more than 5 KU.

Example formulation: $TiO_2$ (solids basis): 24.35 wt. %; water: 46.39 wt. %; propylene glycol 2.59 wt. %; latex (solids basis) 22.76%; ammonium hydroxide: 0.04 wt. %; preservative: 0.10 wt. %; control additive (solvent): 1.14 wt. %; derivative (56% active): 0.40 wt. %; thickener: 2.23 wt. %. PVC: 22.1%. VOC: <50 g/L. Final KU: 98.6.

Wet Scrub Resistance/ASTM 2486 Modified:

Wet scrub resistance based on a modified version of ASTM-2486-00, method B; modified to % weight loss, is performed for each paint formulation. Paints are applied to Leneta P-121-10N plastic panels using a 13-cm wide, 10-mil wet film applicator and dried under ambient conditions for five days prior to testing. The coated panels are then cut into strips (16.5 cm×5.7 cm, two per drawdown). The strips are weighed prior to testing. Two samples at a time are placed on a Gardner Company scrub tester with approximately a 2" gap between the samples and taped to secure panels to the machine. A spacer is placed over the samples to maintain the scrub brush pathway and further secure the samples. A scrub brush (8 cm×3 cm), preconditioned in room temperature water, is inserted into the holder. Scrub compound (10 g, supplied by Leneta Company as "ASTM-2486 scrub compound") is applied evenly to the brush. Water (5 g) is placed into the gap between the samples. Samples are tested to 1200 cycles. Additional scrub compound (10 g) and water (5 g) are reapplied every 300 cycles. The strips are then rinsed under tepid water and dried for 24 h. The strips are reweighed and the % coating removed is determined.

Gloss Determination—60°/20°—ASTM D523

Paints are applied to Leneta P-121-10N plastic panels using a wet film applicator (13 cm×10 mil) and dried under ambient conditions for 5 days prior to testing. Gloss is measured with an ASTM accepted glossmeter (Gardco).

Results:

Sample A12-16 performs as well as the control surfactants as a paint additive (see Table 11).

TABLE 11

Performance as a Latex Paint Additive

| | 60° gloss | 20° gloss | % coating removed, scrub | rating |
|---|---|---|---|---|
| Control 1 | 48.6 | 9.4 | 2.12 | — |
| Control 2 | 51.6 | 11.2 | 2.35 | — |
| A12-16 | 52.3 | 11.5 | 2.30 | equal |

Control 1: ethoxylated (12 EO) saturated $C_{12}$ alcohol
Control 2: ethoxylated (15 EO) saturated $C_{12}$ alcohol Emulsion Polymerization Surfactant Screen:

A reaction kettle is charged with sodium bicarbonate (0.50 g), water (225 g), and seed latex (30 g) and the mixture is heated to and held at 83° C. under nitrogen with stirring at 200 rpm. In a 1-L beaker, surfactant A12-22 (0.50% active surfactant based on total monomer) and water (150 g) are combined and stirred. Methyl methacrylate (255 g), butyl acrylate (235 g), and methacrylic acid (10 g) are combined in an Erlenmeyer flask and mixed. The monomer mixture is added to the beaker containing water and A12-22 with increasing agitator speed, and the resulting mixture is stirred 10 min. or until completely emulsified to give a monomer emulsion. Separately, two other mixtures are prepared: an initiator shot mixture of ammonium persulfate (1.0 g) in water (20 g), and a cofeed mixture of ammonium persulfate (2.70 g), sodium bicarbonate (1.50 g), and water (75 g); the total amount of initiator used is 0.74% based on monomers. The initiator shot is charged to the 83° C. reaction kettle dropwise over 1 min, then held for 10 min. The monomer emulsion is then fed to the kettle at 2.1 mL/min. for 10 min. The feed rate of the monomer emulsion is increased to 4.2 mL/min., and the cofeed mixture is started at 0.37 mL/min. Total addition time is 3 h, during which particle size and temperature are monitored. After addition of the monomer emulsion is complete, a water wash (50 g) is started, and heating at 83° C. continues for 1 h. The product is cooled. The pH is adjusted to 7.5 with dilute ammonium hydroxide solution. A preservative is added, and the mixture is filtered. Results appear in Table 12. The latex formulated using A12-22 is considered equal to the control and suitable for use in formulating a latex paint.

TABLE 12

Evaluation as a Surfactant in Emulsion Polymerization

| | surfactant level in EP (%) | initiation kick-off | coagulum (%) | freeze/thaw result | particle size (nm) |
|---|---|---|---|---|---|
| Control | 0.50 | fast | 0.03 | fluid | 276 |
| A12-22 | 0.50 | fast | <0.01 | fluid | 286 |

A12-22: $C_{12}$ alcohol (30 EO) ethoxylate.

The preceding examples are meant only as illustrations; the following claims define the invention.

We claim:

1. A fatty alcohol alkoxylate having the general structure:

R—CH=CH—(CH$_2$)$_7$—CH$_2$O-(AO)$_n$—H wherein R is H or C$_2$ alkyl; AO is an oxyalkylene group; and n, which is the average number of oxyalkylene groups, has a value within the range of 1 to 50 wherein when R is C$_2$ alkyl, the alkoxylate has at least 1 mole % of trans-$\Delta^9$ unsaturation.

2. A liquid surfactant composition comprising the alkoxylate of claim 1, wherein the surfactant can be processed, formulated, or both at a higher actives level compared with that of a similar composition comprising a saturated analog of the alkoxylate.

3. A mixture comprising water and from 1 to 80 wt %, based on the amount of mixture, of the alkoxylate of claim 1.

4. A fatty alcohol ethoxylate of claim 1.

5. The fatty alcohol ethoxylate of claim 4 wherein n has a value within the range of 1 to 20.

6. A mixture comprising water and from 1 to 80 wt. %, based on the amount of mixture, of the ethoxylate of claim 4.

7. A monounsaturated fatty alcohol ethoxylate of claim 4 having at least one isotropic clear phase over an increased actives level range when compared with that of a saturated analog of the monounsaturated fatty alcohol ethoxylate.

8. The fatty alcohol ethoxylate of claim 7 comprising isotropic and/or lamellar phases at any actives level from 0 to 100%.

9. The fatty alcohol ethoxylate of claim 7 comprising an isotropic clear phase at any actives level from 0 to 100%.

10. A mixture comprising water and from 1 to 80 wt. %, based on the amount of mixture, of the ethoxylate of claim 7.

11. A nonionic emulsifier for agricultural compositions comprising the alkoxylate of claim 1.

12. A nonionic emulsifier for agricultural compositions comprising the ethoxylate of claim 4.

13. An agricultural solvent comprising the alkoxylate of claim 1.

14. An agricultural solvent comprising the ethoxylate of claim 4.

15. An aqueous hard surface cleaner comprising the alkoxylate of claim 1.

16. An aqueous hard surface cleaner comprising the ethoxylate of claim 4.

17. A paint or coating additive composition comprising the alkoxylate of claim 1.

18. A paint or coating additive composition comprising the ethoxylate of claim 4.

19. A laundry detergent formulation comprising the alkoxylate of claim 1.

20. A laundry detergent formulation comprising the ethoxylate of claim 4.

21. A foamer, foam additive, or dispersant for use in gypsum, concrete, or fire-fighting applications comprising the alkoxylate of claim 1.

22. A foamer, foam additive, or dispersant for use in gypsum, concrete, or fire-fighting applications comprising the ethoxylate of claim 4.

23. A surfactant composition for use in enhanced oil recovery, comprising the alkoxylate of claim 1.

24. A surfactant composition for use in enhanced oil recovery, comprising the ethoxylate of claim 4.

* * * * *